US012569587B2

(12) United States Patent　　　　　(10) Patent No.: US 12,569,587 B2
Winterton　　　　　　　　　　　　　(45) Date of Patent: Mar. 10, 2026

(54) METHODS FOR DISINFECTING CONTACT LENSES WITH A MANGANESE-COATED DISC, AND RELATED CONTACT LENS TREATMENT SYSTEMS

(71) Applicant: Better Vision Solutions LLC, Keller, TX (US)

(72) Inventor: Lynn Winterton, Keller, TX (US)

(73) Assignee: Better Vision Solutions LLC, Alpharetta, GA (US)

( * ) Notice: Subject to any disclaimer, the term of this patent is extended or adjusted under 35 U.S.C. 154(b) by 0 days.

(21) Appl. No.: 18/334,450

(22) Filed: Jun. 14, 2023

(65) Prior Publication Data

US 2023/0321311 A1　　Oct. 12, 2023

Related U.S. Application Data

(62) Division of application No. 16/203,721, filed on Nov. 29, 2018, now Pat. No. 11,717,591.

(51) Int. Cl.
A61L 12/12　　　(2006.01)
A61L 12/08　　　(2006.01)
(52) U.S. Cl.
CPC ........... A61L 12/124 (2013.01); A61L 12/086 (2013.01); A61L 12/088 (2013.01)
(58) Field of Classification Search
CPC .... A61L 12/124; A61L 12/086; A61L 12/088; A61L 12/128; B01J 23/34; B01J 35/1009; B01J 35/1042; B01J 37/0215
See application file for complete search history.

(56) References Cited

U.S. PATENT DOCUMENTS

| | | | |
|---|---|---|---|
| 3,423,330 A | 1/1969 | Start et al. | |
| 3,873,696 A | 3/1975 | Randeri et al. | |
| 4,414,127 A | 11/1983 | Fu | |
| 4,585,488 A | 4/1986 | Giefer | |
| 5,431,879 A * | 7/1995 | Heyl | A61L 2/18 |
| | | | 422/312 |
| 5,468,448 A * | 11/1995 | Nicolson | A01N 59/00 |
| | | | 514/840 |
| 5,523,012 A | 6/1996 | Winterton et al. | |
| 6,004,469 A | 12/1999 | Sanders et al. | |
| 6,945,389 B2 | 9/2005 | Scherer et al. | |
| 7,790,128 B2 | 9/2010 | Parrish | |

(Continued)

FOREIGN PATENT DOCUMENTS

| | | | |
|---|---|---|---|
| EP | 0436466 | 7/1991 | |
| JP | H03278837 | * 12/1991 | A61L 2/18 |

(Continued)

OTHER PUBLICATIONS

Translated sections of Sakai (Year: 1991).*

(Continued)

*Primary Examiner* — Brendan A Hensel
(74) *Attorney, Agent, or Firm* — Merchant & Gould P.C.

(57)　　　　　ABSTRACT

Contact lens treatment systems and methods for disinfecting contact lenses are described. These systems and methods utilize a coated catalytic disc, which contains a support disc and a manganese oxide present on at least a portion of the support disc. The coated catalytic disc contains 300 μg to 1800 μg of manganese, often in the form of manganese dioxide.

20 Claims, 7 Drawing Sheets

(56) References Cited

U.S. PATENT DOCUMENTS

| | | | |
|---|---|---|---|
| 8,757,367 | B2 | 6/2014 | Winterton et al. |
| 9,532,632 | B2 | 1/2017 | Winterton et al. |
| 2010/0310429 | A1 | 12/2010 | Kanner |
| 2011/0114517 | A1 | 5/2011 | Minick et al. |
| 2013/0287677 | A1 | 10/2013 | Zhou et al. |
| 2015/0099688 | A1 | 4/2015 | Smith et al. |
| 2019/0168158 | A1 * | 6/2019 | Lee ........................ B01J 23/745 |
| 2020/0321622 | A1 | 10/2020 | Sharman et al. |

FOREIGN PATENT DOCUMENTS

| | | |
|---|---|---|
| WO | WO 2016/182854 | 11/2016 |
| WO | WO 2018/005052 | 1/2018 |

OTHER PUBLICATIONS

Kappenstein et al., "Catalytic Decomposition of $H_2O_2$ Comparison of Unsupported and Alumina Supported Manganese Oxide Catalysts," http://www.ee.surrey.ac.uk/SSC/H2O2CONF/ckappenstein.htm, 2003, 5 pages.

Mooi et al., "Catalytic Decomposition of Hydrogen Peroxide Over Supported Oxides of Manganese," Department of Chemistry Northwestern University, Evanston, IL, Communications to the Editor, Book Reviews, Sep. 1950, vol. 72, pp. 4333-4334.

Russo et al., "Hydrogen Peroxide Decomposition on Manganese Oxide Supported Catalyst: From Batch Reactor to Continuous Microreactor," Ind. Eng. Chem. Res., 2013, 52, pp. 7668-7676.

European Search Report extended report in EP19208191 dated May 14, 2020, 9 pages.

* cited by examiner

116

116

METHODS FOR DISINFECTING CONTACT LENSES WITH A MANGANESE-COATED DISC, AND RELATED CONTACT LENS TREATMENT SYSTEMS

REFERENCE TO RELATED APPLICATION

This application is a divisional application of co-pending U.S. patent application Ser. No. 16/203,721, filed on Nov. 29, 2018, now U.S. Pat. No. 11,717,591, the disclosure of which is incorporated herein by reference in its entirety.

FIELD OF THE INVENTION

The present disclosure concerns methods for disinfecting contact lenses and contact lens treatment systems, and more particularly relates to the use of a manganese-coated catalytic disc in such methods and systems.

BACKGROUND OF THE INVENTION

Contact lens treatment systems of various styles and functionality are utilized for storing, cleaning and/or disinfecting contact lenses. In some lens containment and care systems, a hydrogen peroxide ($H_2O_2$) based disinfecting solution is used, in which the contact lenses to be cleaned and/or disinfected are deposited in contact with the hydrogen peroxide disinfecting solution for a certain period of time, such that cleaning and/or disinfecting of the contact lenses can take place to a satisfactory extent. The contact lens treatment systems utilized for cleaning and/or disinfecting of contact lenses typically contain a lens basket, which opens to receive the contact lenses to be cleaned and closes to retain the lenses during treatment. The lens basket can be integrated as part of the cap, which can be attached to a suitable container. Before the cap is placed onto the container, the container is dosed with a desired amount of the hydrogen peroxide disinfecting solution. The contact lens basket containing the lenses to be treated is immersed into the hydrogen peroxide disinfecting solution in the container, and the container is closed by securing the cap onto the container. Conventionally, a platinum disc is present in the container, often secured to the cap and lens basket, to decompose the hydrogen peroxide.

It would be beneficial to develop an improved contact lens treatment system for disinfecting contact lenses. Accordingly, it is to this end that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

One aspect of this invention is directed to a coated catalytic disc, and in this aspect, the coated catalytic disc can comprise a support disc, and a manganese oxide on at least a portion of the support disc. The coated catalytic disc can contain from about 300 μg to about 1800 μg of manganese.

Another aspect of this invention is directed to a making the coated catalytic disc, and in this aspect, the method can comprise contacting a support disc with a coating composition comprising a binder, a manganese oxide, and a diluent, and drying to form the coated catalytic disc.

Methods for disinfecting a contact lens and contact lens disinfecting systems also are encompassed herein. For instance, a typical method for disinfecting a contact lens can comprise immersing the contact lens in a volume of a disinfecting solution comprising from about 1.5 to about 5 vol % $H_2O_2$ in the presence of any of the coated catalytic discs disclosed herein. A representative contact lens disinfecting system can comprise (a) a container configured to receive a cleaning solution, (b) a cap removably attachable to the container, and (c) any of the coated catalytic discs disclosed herein.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description of specific aspects presented herein.

DEFINITIONS

Figure 1:
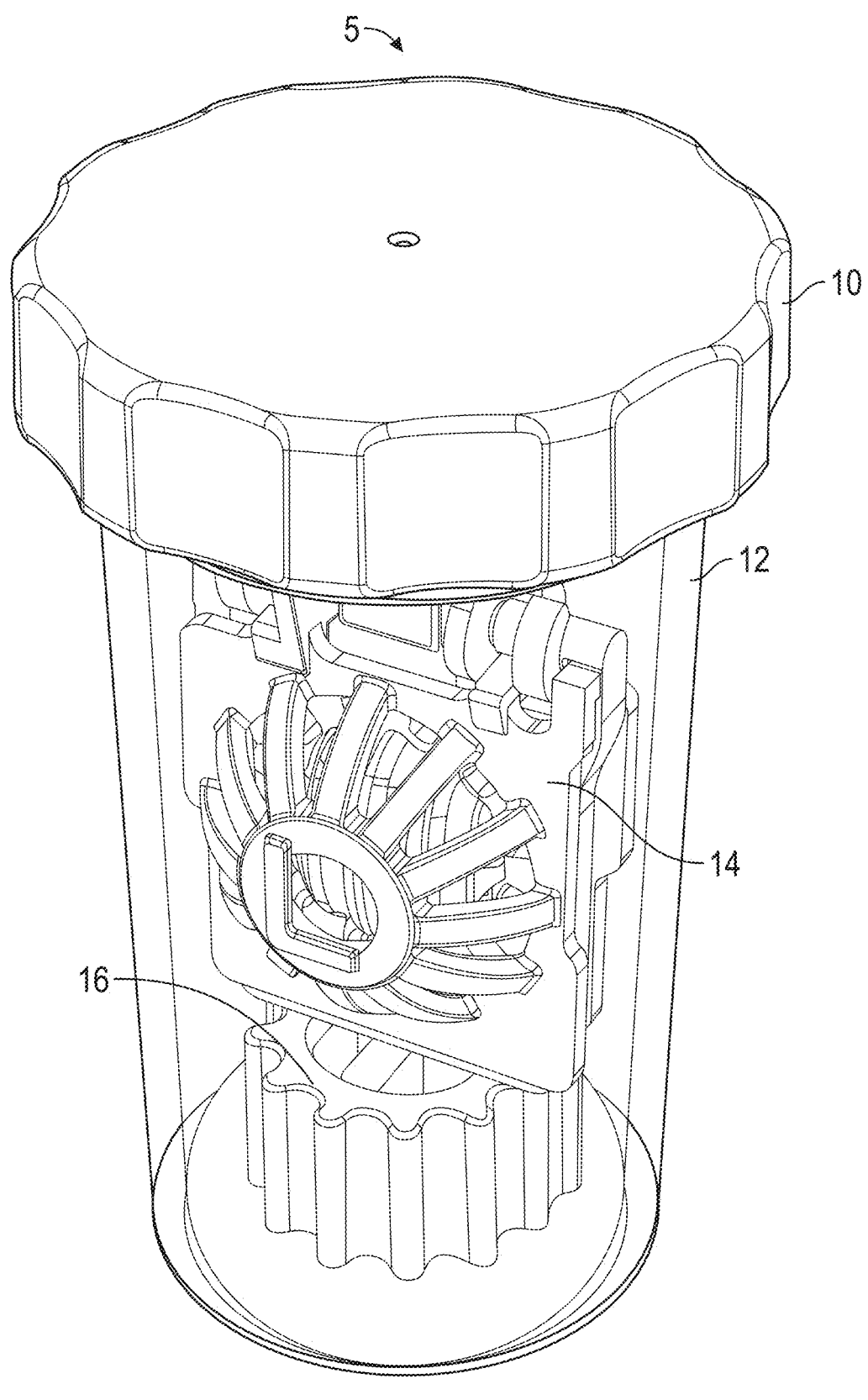
FIG. 1 illustrates a top and front perspective view of a contact lens disinfecting system consistent with an aspect of this invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and/or feature disclosed herein, all combinations that do not detrimentally affect the products, compositions, systems, and methods described herein are contemplated with or without explicit description of the particular combination. Additionally, unless explicitly recited otherwise, any aspect and/or feature disclosed herein can be combined to describe inventive features consistent with the present disclosure.

In this disclosure, while products, compositions, systems, and methods are often described in terms of "comprising" various components, materials, devices, or steps, the products, compositions, systems, and methods also can "consist essentially of" or "consist of" the various components, materials, devices, or steps, unless stated otherwise.

The terms "a," "an," and "the" are intended to include plural alternatives, e.g., at least one. For instance, the disclosure of "a contact lens" is meant to encompass one or more than one contact lens (e.g., two contact lenses), unless otherwise specified. Herein, "contact lens" is used generically to encompass any ophthalmic lens.

The term "about" means that amounts, sizes, formulations, parameters, and other quantities and characteristics are not and need not be exact, but may be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

Various numerical ranges are disclosed herein. When a range of any type is disclosed or claimed, the intent is to disclose or claim individually each possible number that such a range could reasonably encompass, including end points of the range as well as any sub-ranges and combinations of sub-ranges encompassed therein, unless otherwise specified. As a representative example, the present disclosure recites that the coated catalytic disc can contain from about 0.01 wt. % to about 0.3 wt. % manganese (Mn) in certain aspects. By a disclosure that the amount of manganese can be in a range from about 0.01 wt. % to about 0.3 wt. %, the intent is to recite that the manganese content can be any amount within the range and, for example, can be equal to about 0.01, about 0.02, about 0.04, about 0.06, about 0.08, about 0.1, about 0.15, about 0.2, about 0.25, or about 0.3 wt. % manganese. Additionally, the amount of manganese can be within any range from about 0.01 wt. % to about 0.3 wt. % (for example, the amount of manganese can be in a range from about 0.02 wt. % to about 0.2 wt. %), and this also includes any combination of ranges between about 0.01 wt. % and about 0.3 wt. %. Further, in all instances, where "about" a particular value is disclosed, then that value itself is disclosed. Thus, the disclosure of an amount of manganese from about 0.01 wt. % to about 0.3 wt. % also discloses an amount of manganese from 0.01 wt. % to 0.3 wt. % (for example, from 0.02 wt. % to 0.2 wt. %), and this also includes any combination of ranges between 0.01 wt. % and 0.3 wt. %. Likewise, all other ranges disclosed herein should be interpreted in a manner similar to this example.

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are peroxide-based contact lens treatment systems and methods for disinfecting contact lenses. Many conventional systems and methods utilize a hydrogen peroxide solution for disinfection, and a platinum disc to neutralize or decompose the hydrogen peroxide. Platinum, however, is a very rare element, and thus it would be beneficial to develop systems and methods in which the platinum can be replaced with another catalytic material that is more readily available. Further, there are applications for platinum in which there is no suitable alternative, so with a finite supply, there is a need to find an adequate substitute in applications where platinum can be replaced with another catalytic material, with no decrease in performance. Unexpectedly, it was found that a manganese oxide coated disc—as formulated and prepared as described herein—can replace the platinum disc in contact lens treatment systems and methods of disinfecting contact lenses, and with no decrease in performance. Further, platinum is very expensive, and thus a less costly alternative utilizing a manganese oxide would be beneficial to both manufactures and consumers.

Advantageously, the systems and methods disclosed herein utilize a manganese oxide coated catalytic disc, instead of a platinum disc, with surprisingly similar performance in contact lens treatment systems and in methods for disinfecting contact lenses.

Coated Catalytic Discs

The coated catalytic disc consistent with aspects of this invention can comprise a support disc, and a manganese oxide present on at least a portion of the support disc. Generally, a uniform coating of the manganese oxide is applied to the support disc, such that the manganese oxide is present on a large portion of the support disc, and in some instances, substantially all of the support disc is coated with the manganese oxide. Thus, the manganese oxide can be present on at least about 50%, at least about 85%, at least about 90%, at least about 95%, at least about 98%, or at least about 99%, of the surface area of the support disc.

The coated catalytic disc typically contains from about 300 μg to about 1800 μg of manganese. This amount is based on elemental manganese, not the manganese oxide. In one aspect, the coated catalytic disc can contain from about 400 μg to about 1300 μg of manganese, while in another aspect, the coated catalytic disc can contain from about 600 μg to about 1400 μg of manganese, and in yet another aspect, from about 500 μg to about 1500 μg of manganese. Other appropriate ranges for the amount of manganese present on the coated catalytic disc are readily apparent from this disclosure.

While not limited thereto, the coated catalytic disc can contain from about 0.01 wt. % to about 0.3 wt. % manganese. The weight percentage is determined by dividing the total weight of manganese (elemental) on the coated catalytic disc by the weight of the support disc. In some aspects, the coated catalytic disc can contain from about 0.02 wt. % to about 0.25 wt. % manganese; alternatively, from about 0.02 wt. % to about 0.2 wt. % manganese; alternatively, from about 0.05 wt. % to about 0.25 wt. % manganese; or alternatively, from about 0.05 wt. % to about 0.2 wt. % manganese. Other appropriate ranges for the percentage amount of manganese present on the coated catalytic disc are readily apparent from this disclosure.

The volume, surface area, and weight of the coated catalytic disc (or the support disc) are not particularly limited. Generally, however, the volume of the coated catalytic disc (or the support disc) falls within a range from about 0.5 cc to about 1 cc, from about 0.6 cc to about 0.9 cc, or from about 0.6 cc to about 0.8 cc. As one of skill in the art would readily recognize, the volume can depend upon the geometry (shape and size) of the disc. Likewise, the surface area of the coated catalytic disc (or the support disc) is not limited to any particular range, but often falls within a range from about 2 $cm^2$ to about 20 $cm^2$, from about 4 $cm^2$ to about 14 $cm^2$, from about 6 $cm^2$ to about 12 $cm^2$, or from about 7 $cm^2$ to about 11 $cm^2$. As evidenced by the low surface area, the support disc has no internal porosity, or substantially no internal porosity. In addition to disc geometry, the density of the support disc can impact the weight of the coated catalytic disc (or the support disc). Illustrative and non-limiting ranges for the weight of the coated catalytic disc (or the support disc) include from about 0.2 g to about 4 g, from about 0.3 g to about 2 g, from about 0.5 g to about 1.5 g, or from about 0.5 g to about 1 g. Additionally or alternatively, the coated catalytic disc (or the support disc) can have a specific surface area (in units of $cm^2/g$) in a range from about 1 $cm^2/g$ to about 20 $cm^2/g$, such as, for instance, from about 2 $cm^2/g$ to about 18 $cm^2/g$, from about 5 $cm^2/g$ to about 15 $cm^2/g$, or from about 7 $cm^2/g$ to about 12 $cm^2/g$. Other appropriate ranges for the volume, surface area, weight, and specific surface area of the coated catalytic disc (or the support disc) are readily apparent from this disclosure.

The coated catalytic disc can comprise a manganese oxide deposited on at least a portion of the support disc. Any suitable manganese oxide can be used, non-limiting examples of which can include manganese (II) oxide (MnO), manganese (III) oxide ($Mn_2O_3$), manganese dioxide ($MnO_2$), and the like, as well as any combination thereof. In particular aspects of this invention, the manganese oxide can comprise (or consist essentially of, or consist of) manganese dioxide ($MnO_2$).

The support disc can be constructed of any material suitable for supporting manganese. Generally, the support disc is prepared from (often injection molded from) a polymer. Thus, while not being limited thereto, the support disc can comprise a polyamide (PA), a polyphenylene oxide (PPO), a polyphenyl ether (PPE), a polypropylene (PP), a polyethylene (PE), a polystyrene (PS), and the like, as well as any mixture or combination thereof. A particular suitable polymer type for the support disc is a NORYL resin, although not limited thereto.

Methods for Making the Coated Catalytic Disc

Aspects of this invention are directed to methods of making the coated catalytic disc, for example, the coated catalytic disc as described hereinabove. Such methods can comprise contacting a support disc with a coating composition comprising a binder, a manganese oxide, and a diluent; and drying to form the coated catalytic disc. Generally, the features of the methods disclosed herein (e.g., the support disc, the binder, the manganese oxide, the diluent, the conditions under which the support disc and the coating composition are contacted, and the drying conditions, among others) are independently described herein, and these features can be combined in any combination to further describe the disclosed methods. Moreover, other process steps can be conducted before, during, and/or after any of the steps listed in the disclosed methods, unless stated otherwise. Coated catalytic discs prepared by any of these methods also are encompassed herein.

The coating composition can contain a binder, a manganese oxide (e.g., manganese dioxide), and a diluent. Any suitable binder can be used, such as an acrylic polymer, a urethane polymer, or any combination thereof. Likewise, any suitable diluent can be used, such as water, an organic solvent (e.g., mineral spirits, turpentine, an alcohol, etc.), or any combination thereof. In some aspects, the coating composition is a "water-based" coating composition, and the diluent comprises (or consists essentially of, or consists of) water. Generally, the organic solvent is not particularly limited, so long as it does not adversely impact the support disc (e.g., solubilize) or the binder.

While not limited thereto, the coating composition can contain from about 0.05 wt. % to about 5 wt. % of the manganese oxide. The weight percentage is determined by dividing the weight of the manganese oxide by the total weight of the coating composition. In some aspects, the coating composition can contain from about 0.3 wt. % to about 3 wt. % manganese oxide; alternatively, from about 0.5 wt. % to about 2 wt. % manganese oxide; or alternatively, from about 0.1 wt. % to about 1 wt. % manganese oxide. Other appropriate ranges for the percentage amount of manganese oxide present in the coating composition are readily apparent from this disclosure.

Optionally, the coating composition can contain any suitable inert filler, non-limiting examples of which can include carbon black, calcium carbonate, titanium dioxide, a pigment, and the like, as well as combinations thereof. When present, the coating composition can contain from about 0.1 wt. % to about 10 wt. % of the inert filler. The weight percentage is determined by dividing the weight of the inert filler by the total weight of the coating composition. In some aspects, the coating composition can contain from about 0.3 wt. % to about 8 wt. % filler; alternatively, from about 0.5 wt. % to about 4 wt. % filler; or alternatively, from about 1 wt. % to about 3 wt. % filler. Other appropriate ranges for the percentage amount of inert filler present in the coating composition are readily apparent from this disclosure.

In the first step of the process, the support disc can be contacted with the coating composition, which can often be in the form of a mixture or slurry of solids in the diluent. Methods of contacting can include dipping the disc in, immersing the disc in, enrobing the disc with, spraying the disc with, brushing the disc with, or coating the disc with, the coating composition, for example, to form a coating or layer on at least a portion (or all or substantially all) of the support disc. Combinations of more than one method of contacting the disc and the coating composition can be used.

In one aspect, the support disc (or discs) can be enrobed with the coating composition by placing the disc (or discs) under a waterfall of the coating composition to apply a layer of the coating composition on at least a portion (or all or substantially all) of the support disc. Excess coating composition can drip off the disc due to gravity, or be removed by any other suitable technique.

In another aspect, the disc (or discs) can be placed in a mesh basket, which is rotated through a vessel containing the slurry coating composition, thereby dipping or immersing the disc (or discs) in the coating composition. One rotation through the coating composition can be used, but often several rotations are used. Excess coating can drip off the disc due to gravity, or be removed by any suitable technique.

After contacting the support disc with the coating composition, drying is used to form the coated catalytic disc. The wet/coated discs can be dried in a basket or on a rack, although not limited to. Illustrative drying conditions can include a temperature from about 20° C. to about 90° C., or from about 25° C. to about 60° C., at ambient pressure or any suitable sub-atmospheric pressure. Thus, in one aspect, drying can be conducted at ambient temperature and pressure. Higher temperatures can be used, but generally not so high as to adversely impact or decompose the binder or the support disc.

Methods for Disinfecting Contact Lenses

Aspects of this invention are directed to methods for disinfecting a contact lens, and such methods can comprise immersing the contact lens in a volume of a disinfecting solution comprising from about 1.5 vol % to about 5 vol % $H_2O_2$ in the presence of a coated catalytic disc, for example, the coated catalytic disc as described hereinabove. Generally, the features of the methods disclosed herein (e.g., the concentration of $H_2O_2$ in the disinfecting solution, the volume of the disinfecting solution, and the coated catalytic disc, among others) are independently described herein, and these features can be combined in any combination to further describe the disclosed methods. Moreover, other process steps can be conducted before, during, and/or after any of the steps listed in the disclosed methods, unless stated otherwise. For instance, and optionally, an enzyme tablet can be added to the disinfecting solution before immersing the contact lens, or during the immersing in the presence of the coated catalytic disc.

The disinfecting solution generally is configured to disinfect the contact lens. Typically, the disinfecting solution contains from about 1.5 vol % to about 5 vol % $H_2O_2$, but in some aspects of this invention, the disinfecting solution can contain from about 3 vol % to about 4 vol %, or from about 2.5 vol % to about 3.5 vol %, $H_2O_2$. The volume of the disinfecting solution used to treat the contact lens (or lenses) is not particularly limited, and the appropriate volume of the disinfecting solution can be defined by the container (having a removable cap and lens basket) in which the disinfection process is conducted. Nonetheless, representative and non-limiting volumes of the disinfecting solution can range from about 2 mL to about 20 mL in one aspect, from about 5 mL to about 15 mL in another aspect, and from about 8 mL to about 12 mL in yet another aspect.

The coated catalytic disc used in the methods for disinfecting a contact lens can be any coated catalytic disc disclosed herein, for example, comprising a support disc and a manganese oxide present on at least a portion of the support disc, in which the coated catalytic disc contains from about 300 μg to about 1800 μg of manganese. The coated catalytic disc can be configured to neutralize (or decompose) the disinfecting solution (e.g., convert most of the hydrogen peroxide to water and oxygen), typically within a time period that suits the contact lens wearer.

For instance, the contact lens (or lenses) can be immersed for a time period of at least about 2 hr, at least about 4 hr, from about 1 hr to about 12 hr, or from about 2 hr to about 6 hr, although other time intervals can be used. In some aspects, the contact lens (or lenses) can be immersed for a time period sufficient to reduce the $H_2O_2$ concentration of the disinfecting solution to less than 100 ppm, and in some instances, less than 50 ppm (ppm by volume). The disinfecting solution, after neutralization, often can have a pH in a range from about 6 to about 8, or from about 6.5 to about 7.5, but is not limited thereto.

Contact Lens Disinfecting Systems

Various contact lens disinfecting systems are disclosed and described herein. For instance, the contact lens disinfecting system can comprise (a) a container configured to receive a disinfecting solution, (b) a cap removably attachable to the container, and (c) a coated catalytic disc, for example, the coated catalytic disc as described hereinabove. Generally, the features of the contact lens disinfecting system disclosed herein (e.g., the container, the cap, and the coated catalytic disc, among others) are independently described herein, and these features can be combined in any combination to further describe the disclosed contact lens disinfecting systems. Moreover, other parts or components can be present in the disclosed contact lens disinfecting systems, unless stated otherwise.

The coated catalytic disc (any coated catalytic disc disclosed herein) can be attached to the cap to form a unitary structure or an integrated structure. In some aspects, the disc can be removably attached to the cap, while in other aspects, the disc can be fixedly attached to the cap. Further, the cap can comprise a lens basket for retaining a contact lens (or lenses), and the lens basket can be configured to project into the container. In particular aspects of this invention, the lens basket is positioned between the coated catalytic disc and the top of the cap.

The container and the cap can be constructed of any suitable material (typically, a polymer or plastic material), and have any suitable geometry. For instance, the container can be generally cylindrical in shape. In some aspects of this invention, the cap can be configured to snap onto the container, while in other aspects, the cap can be configured to screw on and off the container. As to the latter option, the container can have an opening with an external threaded portion, and the cap can have an internal threaded portion. If desired, the cap can additionally contain a pressure-relief vent.

Figure 2:
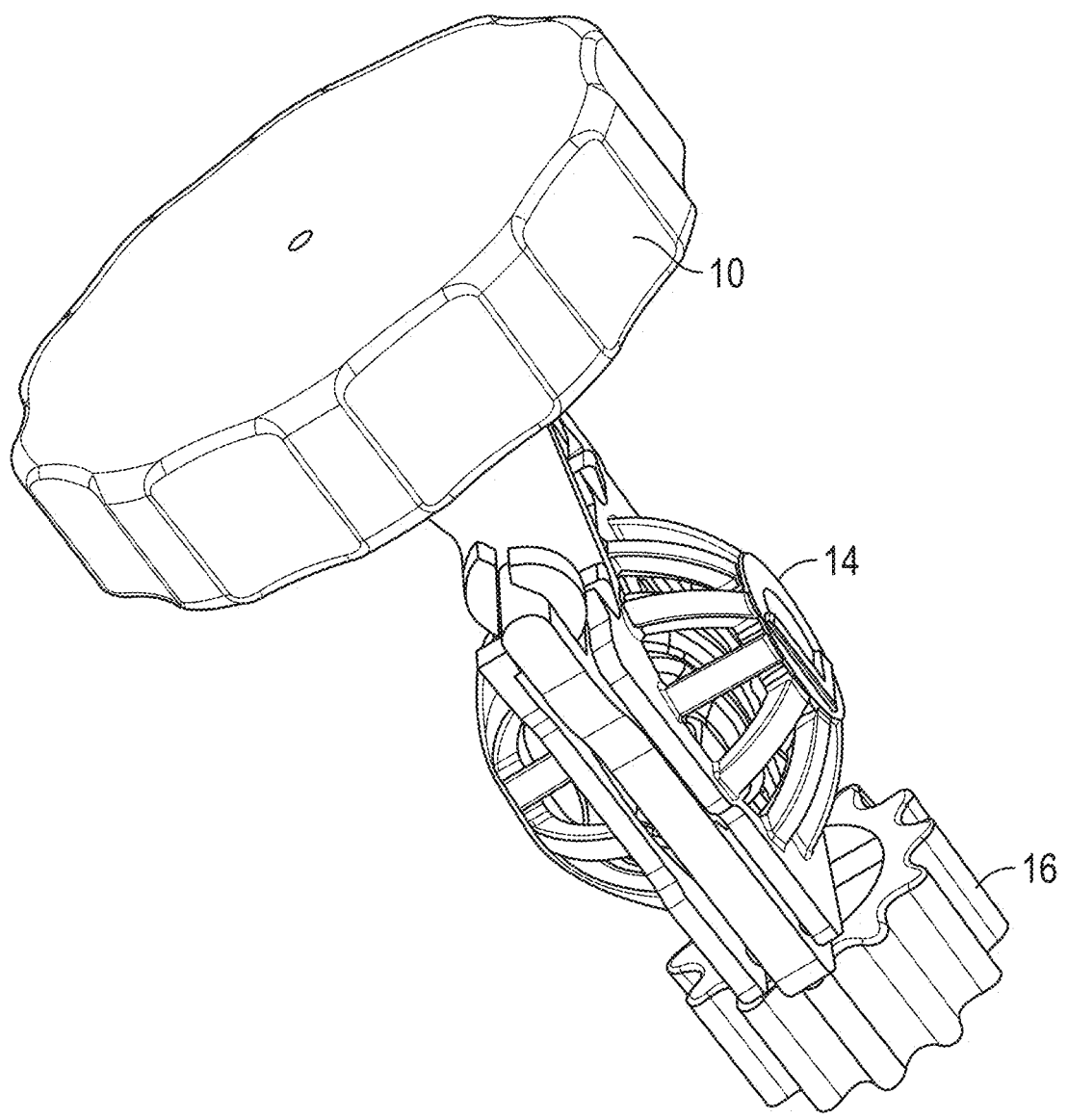
FIG. 2 illustrates a side perspective view of an integrated cap, lens basket, and coated catalytic disc shown in FIG. 1.

A representative contact lens disinfecting system 5 consistent with aspects of this invention is illustrated in FIG. 1. The contact lens disinfecting system 5 includes a cap 10 that connects with a container 12, preferably to form a seal. A lens basket 14 extends from and is supported by the cap 10. In use, the lens basket 14 receives contact lenses and is inserted into the container 12. A coated catalytic disc 16 is connected to the distal free end of the cap 10. FIG. 2 illustrates a unitary construction of the cap 10 with integrated lens basket 14 and coated catalytic disc 16.

In use, the container 12 is filled with a disinfecting solution containing hydrogen peroxide, as described herein. The lens basket 14 is inserted into the disinfecting solution in the container 12 such that the contact lenses are immersed. The hydrogen peroxide disinfects the contact lenses, and the coated catalytic disc 16 neutralizes the hydrogen peroxide.

Figure 3:
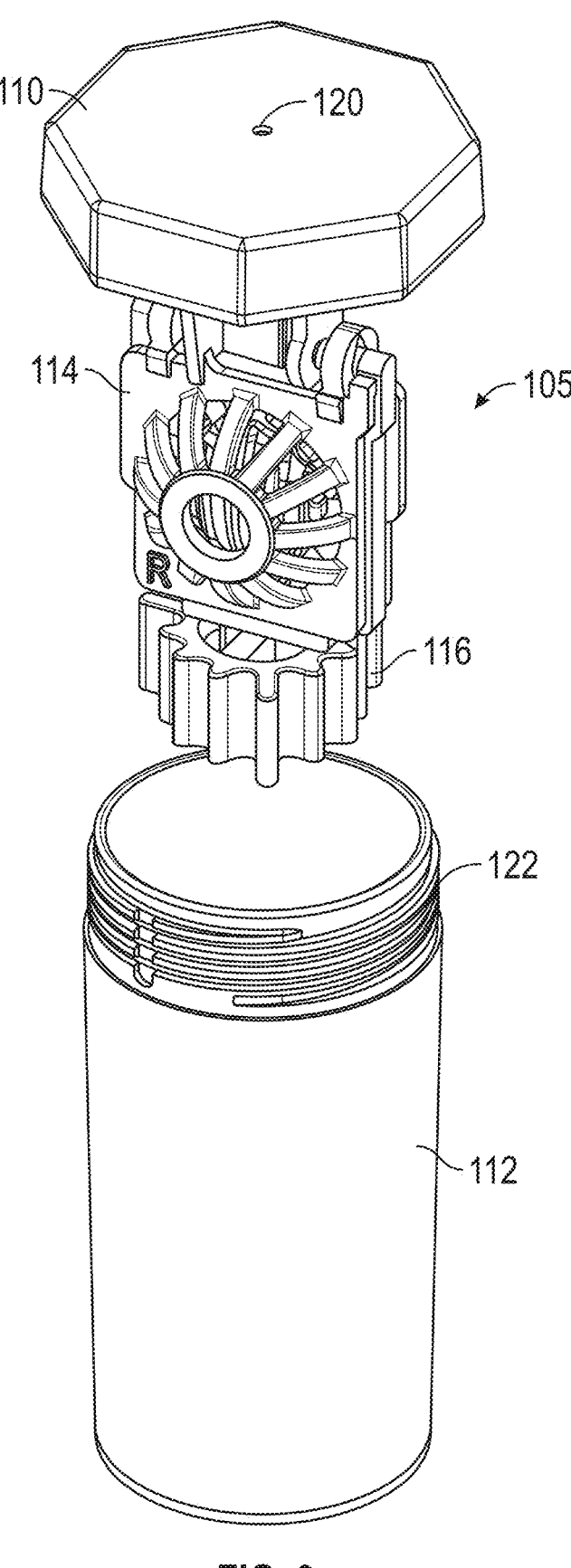
FIG. 3 illustrates a perspective assembly view of a contact lens disinfecting system consistent with another aspect of this invention.
Figure 4:
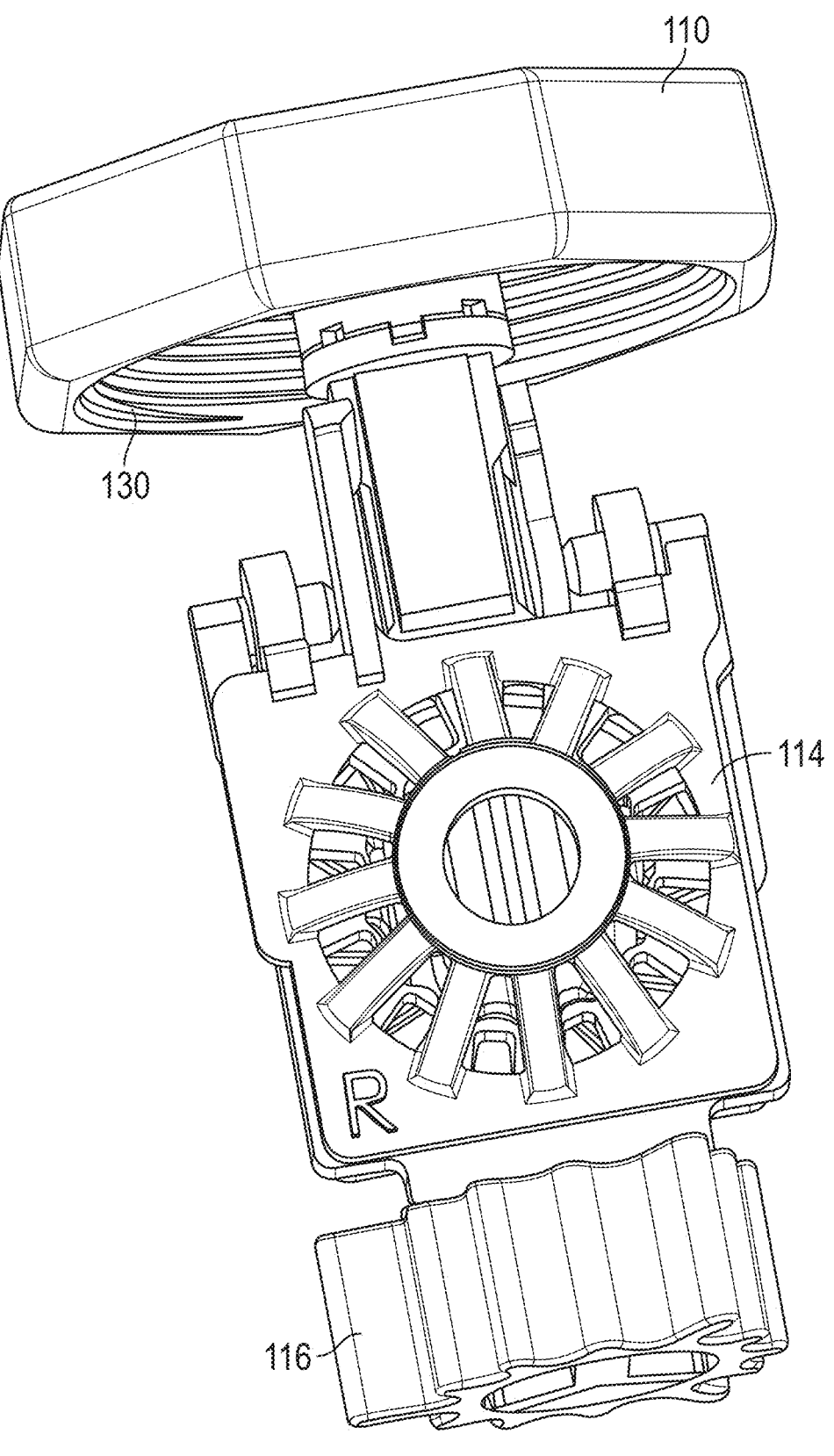
FIG. 4 illustrates a front perspective view of an integrated cap, lens basket, and coated catalytic disc shown in FIG. 3.

Another representative contact lens disinfecting system 105 consistent with aspects of this invention is illustrated in FIG. 3, and includes a cap 110, a container 112, a lens basket 114, and a coated catalytic disc 116. FIG. 4 illustrates a unitary construction of the cap 110 with integrated lens basket 114 and coated catalytic disc 116. The cap 110 can have a pressure-relief vent 120 and an internal threaded portion 130, and the container 112 can have an external threaded portion 122.

Figure 5A:
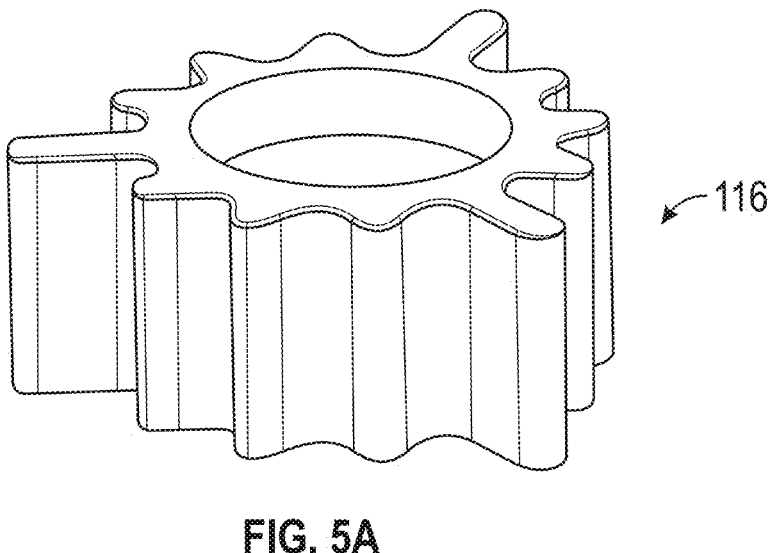
FIGS. 5A-5B are an exploded view and a bottom exploded view, respectively, of the coated catalytic disc shown in FIG. 4.
Figure 5B:
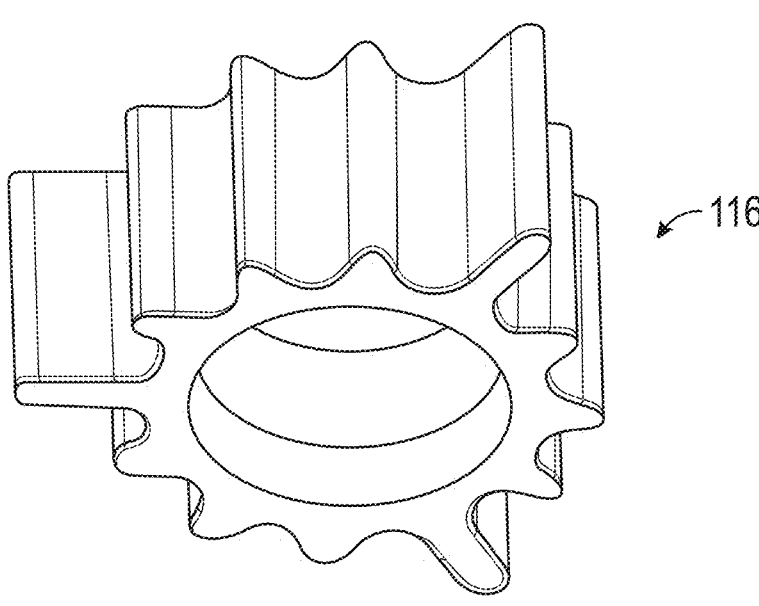

FIGS. 5A-5B show expanded views of the coated catalytic disc 116, and the different geometry as compared to the coated catalytic disc in FIG. 2. Any suitable disc geometry (shape or size) can be used in the contact lens disinfecting system, such as described in U.S. Patent Publication No. 2011/0114517, incorporated herein by reference in its entirety. The use of the coated catalytic disc (containing manganese) is not limited solely to the disinfecting systems disclosed herein, and can be integrated into any conventional contact lens disinfecting system, such as described in U.S. Pat. Nos. 6,945,389, 8,767,367, and 9,532,632, incorporated herein by reference in their entirety.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

Example 1

For Example 1, a manganese coated catalytic disc was prepared using a support disc injection molded from a NORYL resin. The support disc had a surface area of 8.73 $cm^2$, a volume of 0.67 cc, and a weight of approximately 690 mg.

The support disc was placed into a mesh basket, which was rotated several times through a bath containing a water-based coating composition, which a contained a black pigmented acrylic paint and 0.15 wt. % of manganese dioxide. Alternatively, a non-pigmented binder can be used, and an inert filler—such as carbon black—can be used without impacting performance. Excess coating was removed from the coated disc, which was then dried at ambient conditions. The manganese coated catalytic disc contained 1.5 mg of manganese dioxide (1500 μg), which equates to ~950 μg of manganese. The amount of manganese present on the disc can be confirmed by scraping off or removing the coating from the disc, and then performing any suitable metals analysis test.

Figure 6:
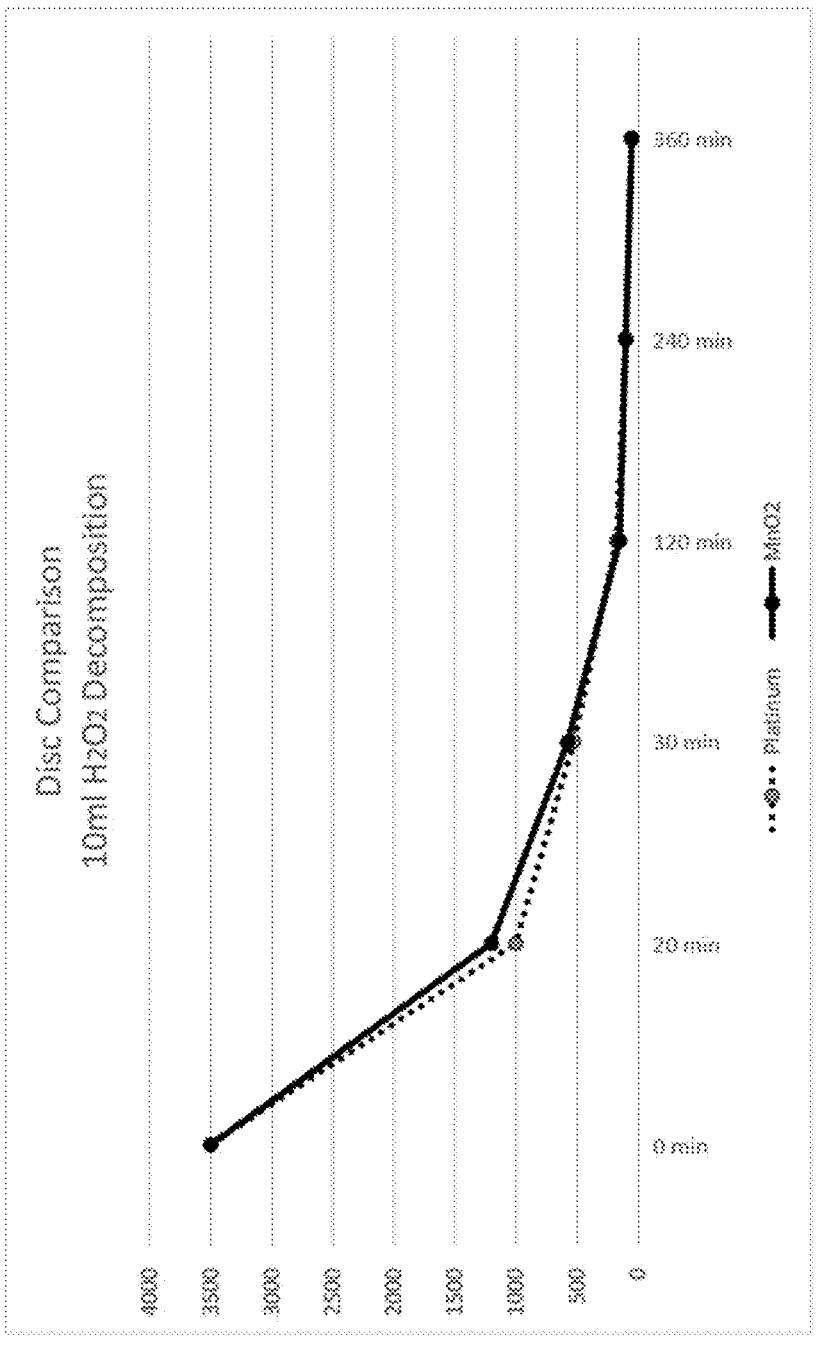
FIG. 6 presents hydrogen peroxide decomposition plots for the platinum disc and manganese oxide disc of Example 1.

The peroxide decomposition performance of the manganese coated catalytic disc was compared to a standard platinum disc (AO Disc) by placing the respective discs in 10 mL of a nominal 3 vol % $H_2O_2$ cleaning solution (ClearCare), and monitoring the ppm of $H_2O_2$ (ppm by volume) over a 6-hr period. FIG. 6 illustrates the peroxide decomposition results. Unexpectedly, the manganese coated catalytic disc of Example 1 had almost identical peroxide decomposition kinetics as that of the platinum disc, with both reaching 100 ppm $H_2O_2$ after 4 hr and 50 ppm $H_2O_2$ after 6 hr.

Example 2

Example 2 was performed substantially the same as Example 1, except that the manganese coated catalytic disc contained 1 mg of manganese dioxide (1000 μg), which equates to ~630 μg of manganese.

Figure 7:
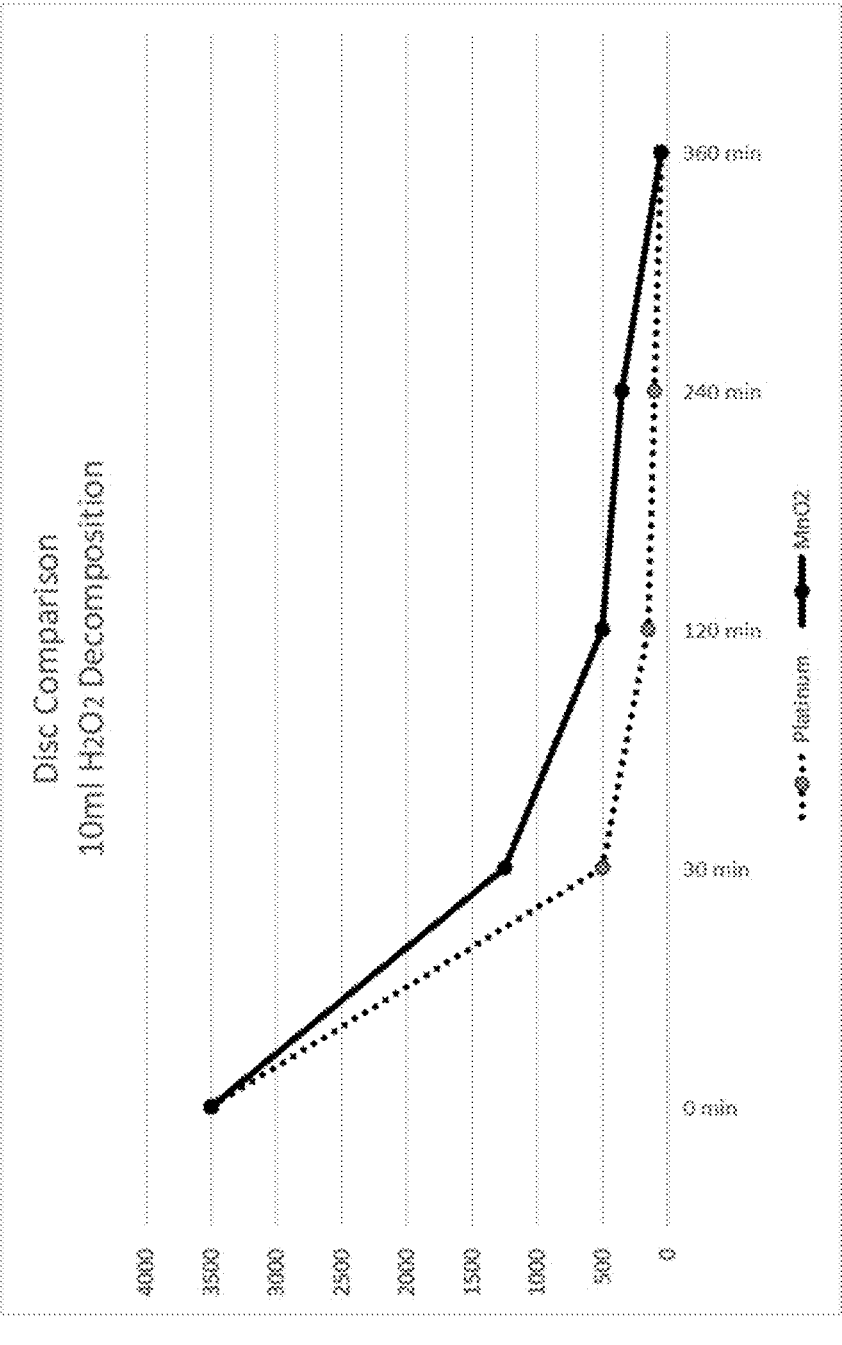
FIG. 7 presents hydrogen peroxide decomposition plots for the platinum disc and manganese oxide disc of Example 2.

As in Example 1, the peroxide decomposition performance of the manganese coated catalytic disc of Example 2 was compared to a standard platinum disc (AO Disc) by placing the respective discs in 10 mL of a nominal 3 vol % $H_2O_2$ cleaning solution (ClearCare), and monitoring the ppm of $H_2O_2$ (ppm by volume) over a 6-hr period. FIG. 7 illustrates the peroxide decomposition results. By using a lower level of manganese, the peroxide decomposition kinetics were slower than that for the platinum disc for times up to 4 hr. However, both discs reached 50 ppm $H_2O_2$ after 6 hr.

Thus, the amount of manganese present on the coated catalytic disc can be varied to impact the peroxide decomposition kinetics. Further, if the surface to volume ratio of the coated catalytic disc is changed, the amount of manganese present on the coated catalytic disc can be varied accordingly.

The longevity of the manganese coated catalytic discs of Examples 1-2 was confirmed to be at least 10 cycles, by repeating the peroxide decomposition tests 10 times. After 10 cycles, a level of less than 100 ppm $H_2O_2$ was reached after 6 hr. Although not tested, it is expected that the longevity would be at least 30 cycles. Moreover, additional filler can be added to the coating composition to promote greater dispersion of the manganese oxide, and to increase effectiveness over 10 or more (or 30 or more) peroxide decomposition cycles.

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of" unless specifically stated otherwise):

Aspect 1. A coated catalytic disc comprising:

a support disc; and a manganese oxide on at least a portion of the support disc;

wherein the coated catalytic disc comprises from about 300 μg to about 1800 μg of manganese.

Aspect 2. The disc defined in aspect 1, wherein the amount of manganese is from about 400 μg to about 1300 μg, or from about 600 μg to about 1400 μg.

Aspect 3. The disc defined in aspect 1 or 2, wherein the manganese oxide comprises manganese (II) oxide (MnO), manganese (III) oxide ($Mn_2O_3$), manganese dioxide ($MnO_2$), or any combination thereof.

Aspect 4. The disc defined in aspect 1 or 2, wherein the manganese oxide comprises manganese dioxide ($MnO_2$).

Aspect 5. The disc defined in any one of aspects 1-4, wherein the support disc comprises a polyamide (PA), a polyphenylene oxide (PPO), a polyphenyl ether (PPE), a polypropylene (PP), a polyethylene (PE), a polystyrene (PS), or any combination thereof.

Aspect 6. The disc defined in any one of aspects 1-5, wherein the coated catalytic disc (or the support disc) has a volume in a range from about 0.5 cc to about 1 cc, or from about 0.6 cc to about 0.9 cc.

Aspect 7. The disc defined in any one of aspects 1-6, wherein the coated catalytic disc (or the support disc) has a surface area in a range from about 2 $cm^2$ to about 20 $cm^2$, from about 4 $cm^2$ to about 14 $cm^2$, or from about 6 $cm^2$ to about 12 $cm^2$.

Aspect 8. The disc defined in any one of aspects 1-7, wherein the coated catalytic disc (or the support disc) weighs from about 0.2 g to about 4 g, from about 0.5 g to about 1.5 g, or from about 0.5 g to about 1 g.

Aspect 9. The disc defined in any one of aspects 1-8, wherein the coated catalytic disc (or the support disc)

has a specific surface area in a range from about 1 $cm^2/g$ to about 20 $cm^2/g$, or from about 5 $cm^2/g$ to about 15 $cm^2/g$.

Aspect 10. The disc defined in any one of aspects 1-9, wherein the coated catalytic disc contains from about 0.01 wt. % to about 0.3 wt. % Mn, from about 0.02 wt. % to about 0.2 wt. % Mn, or from about 0.05 wt. % to about 0.2 wt. % Mn.

Aspect 11. A method of making the coated catalytic disc defined in any one of aspects 1-10, the method comprising:

contacting the support disc with a coating composition comprising a binder, the manganese oxide, and a diluent; and drying to form the coated catalytic disc.

Aspect 12. The method defined in aspect 11, wherein:

the binder comprises an acrylic polymer and/or a urethane polymer; and the diluent comprises water and/or an organic solvent.

Aspect 13. The method defined in aspect 11 or 12, wherein contacting comprises dipping, immersing, enrobing, spraying, brushing, coating, or any combination thereof (to form a coating on the support disc).

Aspect 14. The method defined in any one of aspects 11-13, wherein drying comprises a temperature from about 20° C. to about 90° C., or from about 25° C. to about 60° C., at ambient pressure or any suitable sub-atmospheric pressure.

Aspect 15. The method defined in any one of aspects 11-14, wherein the coating composition comprises from about 0.05 wt. % to about 5 wt. %, or from about 0.1 wt. % to about 1 wt. %, of the manganese oxide.

Aspect 16. The method defined in any one of aspects 11-15, wherein the coating composition further comprises an inert filler.

Aspect 17. The method defined in aspect 16, wherein the coating composition comprises from about 0.1 wt. % to about 10 wt. %, or from about 0.5 wt. % to about 4 wt. %, of the inert filler.

Aspect 18. The coated catalytic disc prepared by the method defined in any one of aspects 11-17.

Aspect 19. A method for disinfecting a contact lens, the method comprising:

immersing the contact lens in a volume of a disinfecting solution comprising from about 1.5 vol % to about 5 vol % $H_2O_2$ in the presence of the coated catalytic disc defined in any one of aspects 1-10 or 18.

Aspect 20. The method defined in aspect 19, wherein the contact lens is immersed for at least 2 hr, from about 1 hr to about 12 hr, or from about 2 hr to about 6 hr (and/or for a time sufficient to reduce the $H_2O_2$ concentration to less than 100 ppm, or less than 50 ppm).

Aspect 21. The method defined in aspect 19 or 20, wherein the disinfecting solution, after neutralization, has a pH in a range from about 6 to about 8, or from about 6.5 to about 7.5.

Aspect 22. The method defined in any one of aspects 19-21, wherein the volume of the disinfecting solution is from about 2 mL to about 20 mL, from about 5 mL to about 15 mL, or from about 8 mL to about 12 mL.

Aspect 23. The method defined in any one of aspects 19-22, wherein the coated catalytic disc is configured to neutralize the disinfecting solution.

Aspect 24. The method defined in any one of aspects 19-23, wherein the disinfecting solution is configured to disinfect the contact lens.

Aspect 25. The method defined in any one of aspects 19-24, wherein the disinfecting solution comprises from about 3 vol % to about 4 vol %, or from about 2.5 vol % to about 3.5 vol. %, $H_2O_2$.

Aspect 26. The method defined in any one of aspects 19-25, wherein an enzyme tablet is added to the disinfecting solution.

Aspect 27. A contact lens disinfecting system comprising:

(a) a container configured to receive a disinfecting solution;

(b) a cap removably attachable to the container; and (c) the coated catalytic disc defined in any one of aspects 1-10 or 18.

Aspect 28. The system defined in aspect 27, wherein the coated catalytic disc is removably attached to the cap.

Aspect 29. The system defined in aspect 27 or 28, wherein the cap further comprises a lens basket for retaining a contact lens, and wherein the lens basket is configured to project into the container.

Aspect 30. The system defined in any one of aspects 27-29, wherein the cap comprises a pressure-relief vent.

Aspect 31. The system defined in any one of aspects 27-30, wherein the cap is configured to snap onto the container.

Aspect 32. The system defined in any one of aspects 27-31, wherein the container comprises an opening with an external threaded portion.

Aspect 33. The system defined in any one of aspects 27-32, wherein the cap comprises an internal threaded portion.

Aspect 34. The system defined in aspect 32 or 33, wherein the cap is configured to screw on and off the container.

What is claimed is:

1. A contact lens disinfecting system comprising:

(a) a container configured to receive a disinfecting solution;

(b) a cap removably attachable to the container; and (c) a coated catalytic disc comprising:

a support disc comprising a polyamide, a polyphenylene oxide, a polyphenyl ether, a polypropylene, a polyethylene, a polystyrene, or any combination thereof; and a coating comprising a binder and a manganese dioxide ($MnO_2$) on at least a portion of the support disc;

wherein the coated catalytic disc comprises from about 300 μg to about 1800 μg of manganese.

2. The system of claim 1, wherein the coated catalytic disc is removably attached to the cap.

3. The system of claim 1, wherein the cap further comprises a lens basket for retaining a contact lens, and wherein the lens basket is configured to project into the container.

4. The system of claim 1, wherein the cap is configured to snap onto the container.

5. The system of claim 1, wherein:

the container comprises an opening with an external threaded portion;

the cap comprises an internal threaded portion; and the cap is configured to screw on and off the container.

6. The system of claim 1, wherein the coated catalytic disc is characterized by:

a volume in a range from about 0.5 cc to about 1 cc;

a surface area in a range from about 2 cm$^2$ to about 20 cm$^2$;

a weight in a range from about 0.2 g to about 4 g;

a specific surface area in a range from about 1 cm$^2$/g to about 20 cm$^2$/g; and from about 0.01 wt. % to about 0.3 wt. % manganese.

7. The system of claim 1, wherein the coated catalytic disc is characterized by:

a volume in a range from about 0.6 cc to about 0.9 cc;

a surface area in a range from about 6 cm$^2$ to about 12 cm$^2$;

a weight in a range from about 0.5 g to about 1 g;

a specific surface area in a range from about 5 cm$^2$/g to about 15 cm$^2$/g; and from about 0.05 wt. % to about 0.2 wt. % manganese.

8. The system of claim 1, wherein the coated catalytic disc contains from about 0.02 wt. % to about 0.2 wt. % manganese.

9. The system of claim 1, wherein the coated catalyst disc comprises from about 600 μg to about 1400 μg of manganese.

10. The system of claim 1, wherein the coated catalytic disc is characterized by:

a volume in a range from about 0.5 cc to about 1 cc;

a surface area in a range from about 2 cm$^2$ to about 20 cm$^2$;

a weight in a range from about 0.2 g to about 4 g; and a specific surface area in a range from about 1 cm$^2$/g to about 20 cm$^2$/g.

11. The system of claim 1, wherein the coated catalytic disc is characterized by:

a volume in a range from about 0.6 cc to about 0.9 cc;

a surface area in a range from about 6 cm$^2$ to about 12 cm$^2$;

a weight in a range from about 0.5 g to about 1 g; and a specific surface area in a range from about 5 cm$^2$/g to about 15 cm$^2$/g.

12. The system of claim 1, wherein:

the coated catalytic disc contains from about 0.01 wt. % to about 0.3 wt. % manganese.

13. The system of claim 12, wherein the coated catalytic disc contains from about 0.05 wt. % to about 0.2 wt. % manganese.

14. The system of claim 12, wherein the coated catalytic disc contains from about 600 μg to about 1400 μg of manganese.

15. The system of claim 12, wherein the coated catalytic disc is removably attached to the cap.

16. The system of claim 12, wherein the cap further comprises a lens basket for retaining a contact lens, and wherein the lens basket is configured to project into the container.

17. The system of claim 1, wherein the binder comprises an acrylic polymer, a urethane polymer, or both.

18. The system of claim 1, wherein the binder comprises an acrylic polymer.

19. The system of claim 1, wherein the coating composition further comprises an inert filler selected from the group consisting of carbon black, calcium carbonate, titanium dioxide, a pigment, or combinations thereof.

20. The system of claim 1, wherein the coating composition comprises a black pigmented acrylic paint.

* * * * *